United States Patent [19]

Daoud et al.

[11] Patent Number: 4,923,444
[45] Date of Patent: May 8, 1990

[54] NEGATIVE PRESSURE MEASUREMENT SYSTEM

[75] Inventors: Adib G. Daoud, San Diego; C. Russell Horres, Jr., Del Mar, both of Calif.

[73] Assignee: Ivac Corporation, San Diego, Calif.

[21] Appl. No.: 286,428

[22] Filed: Dec. 19, 1988

[51] Int. Cl.⁵ ............................................. A61M 37/00
[52] U.S. Cl. .................................. 604/131; 604/246; 73/716; 128/748
[58] Field of Search ................. 128/748, 672–675; 604/118, 131, 140, 246–247, 141, 147; 73/756, 715–716

[56] References Cited

U.S. PATENT DOCUMENTS

| | | | |
|---|---|---|---|
| 3,818,765 | 6/1974 | Eriksen | 73/395 |
| 4,072,056 | 2/1978 | Lee | 73/706 |
| 4,185,641 | 1/1980 | Minior et al. | 128/748 X |
| 4,227,420 | 10/1980 | Lamadrid | 73/756 |
| 4,398,542 | 8/1983 | Cunningham et al. | 128/675 |
| 4,539,998 | 9/1985 | McCord et al. | 128/675 |
| 4,567,181 | 3/1986 | Wallace et al. | 128/675 |
| 4,610,256 | 9/1986 | Wallace | 128/675 |
| 4,656,454 | 4/1987 | Rosenberger | 338/2 |
| 4,658,829 | 4/1987 | Wallace | 128/672 |
| 4,665,754 | 5/1987 | Glenn et al. | 73/727 |
| 4,679,567 | 7/1987 | Hanlon et al. | 128/675 |
| 4,710,744 | 12/1987 | Wamstad | 338/4 |
| 4,715,852 | 12/1987 | Reinicke et al. | 604/131 |
| 4,785,821 | 11/1988 | Udell et al. | 128/748 X |

*Primary Examiner*—Angela D. Sykes
*Attorney, Agent, or Firm*—Fulwider, Patton, Lee & Utecht

[57] ABSTRACT

The negative pressure monitor is intended for use in combination with an IV administration set, for monitoring venous, arterial and other physiological pressure signals. The system provides a coupling mechanism with a sealed vacuum chamber between a fluid chamber in communication with the fluid in line, and the pressure transducer. The vacuum in the coupling mechanism serves not only to communicate pressure changes within the fluid chamber to the pressure transducer, but also functions to maintain the fluid chamber in pressure communication with the pressure transducer.

30 Claims, 1 Drawing Sheet

NEGATIVE PRESSURE MEASUREMENT SYSTEM

BACKGROUND OF THE INVENTION

1. Field of the Invention:

This invention relates generally to fluid pressure measurement devices, and more particularly relates to devices measuring pressure within a fluid line of an IV administration set.

2. Description of Related Art:

In intravenous pressure monitoring systems, fluid pressures at the transducer coupling site can fall to a level below that of atmospheric pressure when the body is positioned lower than the transducer level. Due to a conventional design of the mechanical coupling between the fluid path and the transducer, contact between the fluid path and the transducer may be lost when fluid pressures at the transducer coupling site become negative, resulting in incorrect measurements by the transducer. Placement of the transducer below the level of the body may be impractical, and may also result in a pressure imbalance in the pressure monitoring systems. Manufacturers of physiological pressure systems therefore request that the transducer be level with the body cavity for which the measurement is to be made.

Intravenous delivery systems employing fluid sensors for monitoring the proper condition of the fluid conduit cannot always be accurately leveled with the patient. In order to enable the pressure monitoring system to carry a full range of monitoring functions, a coupling mechanism which does not lose contact with the transducer under negative pressure conditions is desirable. Conventional physiological pressure measurement systems employ coupling "domes" or fluid channels between the fluid path and the transducer. In a typical system, in order to insure adequate signal fidelity during declining pressures (as in the case of the diastolic phase of an arterial pressure, or a negative respiratory induced transient CVP pressure) a displaceable fluid such as water is interposed between the dome diaphragm and the transducer membrane surface. The diaphragm and the transducer membrane surface remain in communication due to the fact that water is an incompressible fluid, and a vacuum in the space between the diaphragm and transducer membrane surface would be created were they to separate.

It would be desirable to provide a coupling mechanism for a negative pressure measurement system which will not lose contact with the transducer under negative pressure conditions which is economical and effective to measure pressure in an IV line, under circumstances where the fluid pressure at the transducer would become negative due to a hydrostatic elevation gradient between the patient and the transducing device.

SUMMARY OF THE INVENTION

Briefly and in general terms, the system of the invention for measuring pressures in an IV fluid line comprises a fluid chamber in communication with the IV fluid line, a first transfer diaphragm forming a wall of the fluid chamber, and a second transfer diaphragm defining a vacuum chamber in combination with the first diaphragm, and serving to communicate pressure changes to a pressure transducer. The vacuum chamber also includes a source for inducing a vacuum in the vacuum chamber. The fluid chamber is contained within a disc body portion of the device, and the pressure transducer is contained in a main body portion which preferably includes a vent channel extending from the vacuum chamber to the vacuum source, and a reference air vent to the pressure transducer to provide a reference ambient pressure. A pressure transfer chamber is also preferably provided between the pressure transducer and the second pressure diaphragm, filled with an incompressible fluid, which is preferably a gel.

The present invention provides for a negative pressure measurement system for use in combination with an IV administration set, for monitoring venous, arterial and other physiological pressure signals. The system provides a coupling mechanism with a sealed vacuum chamber between a fluid chamber in communication with the fluid in line, and the pressure transducer. The vacuum in the coupling mechanism serves not only to communicate pressure changes within the fluid chamber to the pressure transducer, but also functions to maintain the fluid chamber in pressure communication with the pressure transducer.

Other aspects and advantages of the invention will become apparent from the following detailed description, and the accompanying drawing, illustrating by way of example the features of the invention.

DETAILED DESCRIPTION OF THE DRAWINGS

Figure 1:
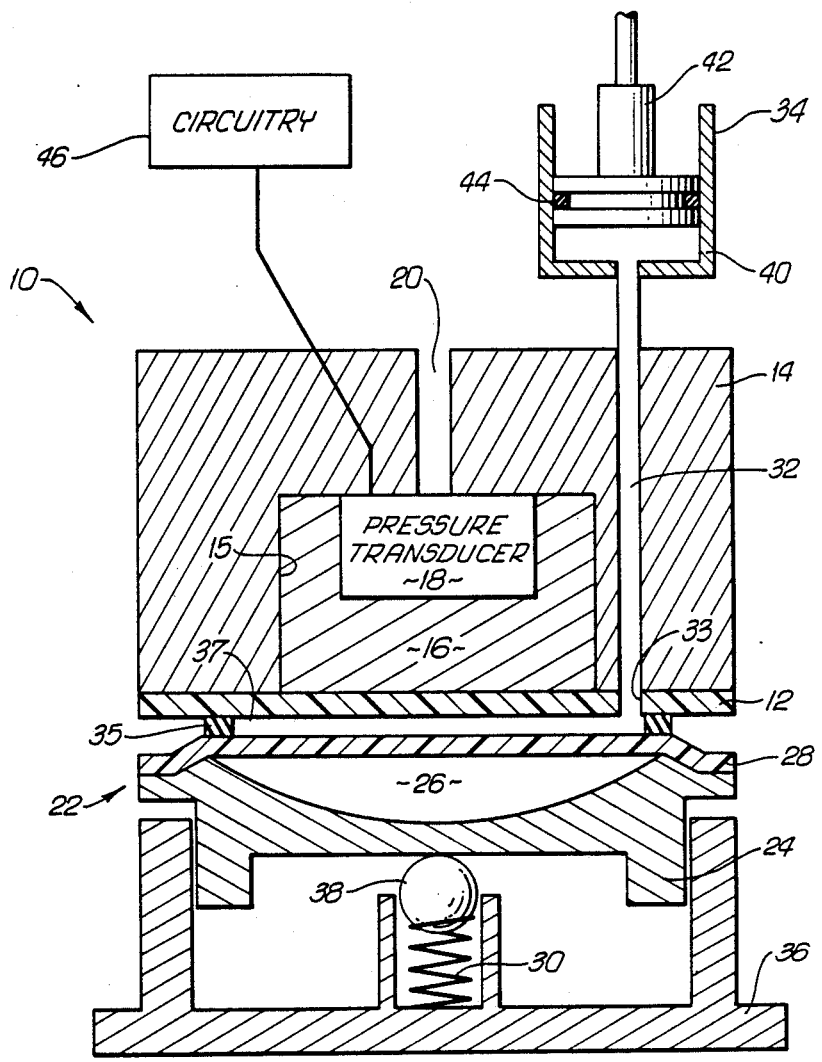
FIG. 1 is a schematic diagram of the negative pressure measurement system.

As is shown in the drawing for purposes of illustration, the invention is embodied in the pressure measurement system particularly adapted for measuring negative pressures falling below ambient pressure in an IV solution administration set. However, the invention is not limited to measurement of negative pressures, and the pressure monitoring system is also useful in sensing the patency or blockage of a fluid path in a fluid line, such as in the IV administration set. Both the negative pressure and the patency of the fluid path may be sensed without regard to elevation of the transducer in relation to a patient. As the vacuum chamber of the coupling mechanism is already at a negative pressure, a negative pressure in the IV set will not cause the transducer to lose contact with the transfer diaphragm. Furthermore, positive pressures will likewise not act to uncouple the transducer from the pressure diaphragm when a sufficient vacuum is achieved in the vacuum. As additional and normal safeguards, means may be provided for biasing the first pressure transfer diaphragm against the second pressure diaphragm against the second pressure transfer diaphragm, and latch means may also be provided for locking the main parts of the pressure monitoring device together.

In accordance with the invention, there is provided a system for measuring pressure in a fluid line; comprising a fluid chamber connected to the fluid lines; a first flexible pressure transfer diaphragm forming one wall of the fluid chamber; a second flexible pressure transfer diaphragm adapted to be placed in sealing engagement with the first diaphragm to form an intermediate vacuum chamber for transferring pressure changes in the fluid chamber from the first diaphragm to the second diaphragm; means for inducing a vacuum in the vacuum chamber for maintaining the first and second diaphragms in sealing engagement; and a pressure transducer responsive to pressure changes transferred by the second diaphragm.

The invention also provides for a system for measuring pressure in a fluid line, comprising a disc body member having a fluid chamber connected to the fluid lines; a first flexible pressure transfer diaphragm secured to the disc body and forming one wall of the fluid chamber; a main body member having a second flexible pressure transfer diaphragm secured thereto and adapted to be placed in sealing engagement with the first diaphragm to form an intermediate vacuum chamber for transferring pressure changes in the fluid chamber from the first diaphragm to the second diaphragm; means for inducing a vacuum in the vacuum chamber for maintaining the first and second diaphragms in sealing engagement; and a pressure transducer responsive to pressure changes transferred by the second diaphragm.

The invention further provides for a pressure coupling means for use in a pressure monitoring assembly for monitoring pressure in a fluid line, comprising a disc body member including a fluid chamber connected to the fluid line and including a first flexible pressure transfer diaphragm forming one wall of the fluid chamber; a main body portion including a second flexible pressure transfer diaphragm adapted to be placed in sealing engagement with the first diaphragm to form an intermediate vacuum chamber for communicating pressure changes in the fluid line from the first diaphragm to the second diaphragm, and means for inducing a vacuum in the vacuum chamber, for maintaining the first and second diaphragms in constant sealing engagement.

As is shown in the drawing, the pressure measuring device 10 includes a main flexible pressure transfer diaphragm 12 secured to the reusable main body 14 having a pressure transfer chamber 15 filled with a substantially incompressible fluid, which is preferably a gel coupling 16 which may be any gelatinous material such as is well known in the art, such as a silicone gel. The pressure transfer chamber also contains the pressure transducer 18, such as a commercially available solid state sensor. Pressure communicated from the transfer diaphragm is transferred to the sensor 18 through the gel coupling. The pressure transducer is also linked to ambient air pressure by the reference air vent 20, in order to permit pressure changes communicated from the main transfer diaphragm to the pressure transducer to be compared with an absolute ambient reference value.

The pressure measuring device also includes a disposable fluid coupling disc 22 having a disc body 24 defining a fluid channel or chamber 26, which is to be connected for communication with the fluid line to be monitored, such as the IV solution tubing. The fluid chamber preferably has an inlet and an outlet, to allow fluid to flow through the chamber, but it is also contemplated that only one access port could be provided in order to still provide pressure information without requiring flow of the IV fluid through the measurement device. The fluid coupling disc also includes a flexible pressure transfer diaphragm 28 secured to the disc body, and preferably forming one of the walls of the fluid chamber. In practice, therefore, the fluid coupling disc can be independently attached or built into the fluid line, so that the main body portion of the pressure measuring device can be simply fastened to the fluid coupling disc portion. A spring mechanism 30 biases the fluid coupling disc into engagement with the main body portion, and a latch mechanism may also be included to secure the fluid coupling disc in position. The bearing or ball 38 contacts the disc body and serves to protect the spring 30.

A vent channel 32 is provided through the main body, communicating through a vent port 33 in the main transfer diaphragm with a vacuum chamber 37 formed when the two pressure transfer diaphragms are engaged in contact. A sealing gasket 35 provides for a spacing between the main and disc transfer diaphragms, and seals the vacuum chamber when vacuum is applied by the vacuum source 34.

The vacuum source may be a piston chamber 40 containing a piston with a seal 44, so that as the piston is moved to a fixed or locked position within the piston chamber, a constant, predetermined vacuum is formed in the piston chamber portion communicating with the vent channel. Other sources of vacuum, such as a regulated vacuum pump, would also be appropriate. As the vacuum applied may not be consistent, means may also be provided for calibrating the reading of the pressure transducer after the vacuum has been applied to the vacuum chamber. This calibration may be, for example, carried out in a microprocessor based circuit such as is indicated generally as the block of circuitry 46.

In the foregoing description, it has been demonstrated that the pressure measurement system of the invention allows monitoring of fluid pressure in a fluid path without the risk of loss of contact of a pressure transducer with the fluid path due to development of a negative pressure in the fluid path, since the invention employs negative pressure in a vacuum chamber in order to maintain communication between the two main portions of the pressure measuring device. The pressure measurement system also allows the disc body portion to be connected in line or built into a fluid path, so that the main body portion containing the pressure transducer can be quickly and simply connected to the disc portion containing the fluid chamber to be monitored.

Since the invention allows for pressure monitoring of a fluid line in an intravenous fluid administration set, problems of upstream occlusion, air in line and line disconnect may also be monitored by the system. The pressure measurement system may be easily installed and involves no cost increase to the disposable fluid path components of conventional IV fluid administration systems. Such a pressure measurement system also now makes it possible to place such a system at any convenient and appropriate location in the IV administration set, and no longer needs to be placed level with the body cavity in which the measurement is to be made.

Although one specific embodiment of the invention has been described and illustrated, it is clear that it is susceptible to numerous modifications and embodiments within the ability of those skilled in the art and without the exercise of the inventive faculty. Thus, it should be understood that variations in form, detail and application of the present invention may be made without departing from the spirit and scope of this invention.

We claim:

1. A system for measuring pressure in a fluid line, comprising:
    a fluid chamber connected to said fluid line;
    a first flexible pressure transfer diaphragm forming one wall of said fluid chamber;
    a second flexible pressure transfer diaphragm placed in sealing engagement with said first diaphragm and forming an intermediate vacuum chamber for transferring pressure changes in said fluid chamber from said first diaphragm to said second diaphragm;

means for inducing a vacuum in said chamber for maintaining said first and second diaphragms in constant sealing engagement; and a pressure transducer coupled to said second diaphragm responsive to pressure changes transferred by said second diaphragm.

2. The system of claim 1, further including a pressure transfer chamber between said second diaphragm and said pressure transducer.

3. The system of claim 1, further including means for sealing said vacuum chamber between said first and second diaphragms.

4. The system of claim 1, further including a vent channel connecting said vacuum chamber to a vacuum source.

5. The system of claim 4, wherein said vacuum source includes means for producing a constant vacuum in said vacuum chamber.

6. The system of claim 1, further including means for biasing said first and second diaphragms together in sealing engagement.

7. The system of claim 1, wherein said fluid chamber comprises a fluid channel having an inlet connected to an IV fluid line, and an outlet connected to the IV fluid line.

8. A system for measuring pressure in a fluid line comprising:

a disc body member having a fluid chamber connected to said fluid line;

a first flexible pressure transfer diaphragm secured to said disc body member and forming one wall of said fluid chamber;

a main body member having a second flexible pressure transfer diaphragm secured thereto placed in sealing engagement with said first diaphragm and forming an intermediate vacuum chamber for transferring pressure changes in said fluid chamber from said first diaphragm to said second diaphragm;

means for including a vacuum in said vacuum in said vacuum chamber for maintaining said first and second diaphragms in constant sealing engagement; and a pressure transducer coupled to said second diaphragm responsive to pressure changes transferred by said second diaphragm.

9. The system of claim 8, further including a pressure transfer chamber between said second diaphragm and said pressure transducer.

10. The system of claim 9, wherein said pressure transfer chamber is filled with a substantially incompressible fluid for communicating said pressure changes from said second transfer diaphragm to said pressure transducer.

11. The system of claim 10, wherein said fluid in said pressure transfer chamber is gelatinous.

12. The system of claim 8, further including means for sealing said vacuum chamber between said first and second diaphragm.

13. The system of claim 8, further including a vent channel connecting said vacuum chamber to a vacuum source.

14. The system of claim 13, wherein said vacuum source includes means for producing a constant vacuum in said vacuum chamber.

15. The system of claim 8, further including means for biasing said first and second diaphragms together in sealing engagement.

16. The system of claim 8, wherein said fluid chamber comprises a fluid channel having an inlet connected to an IV fluid line, and an outlet connected to the IV fluid line.

17. The system of claim 8, further including a reference air vent through said main body portion communicating ambient pressure to said pressure transducer.

18. The system of claim 8, wherein said means for inducing a vacuum comprises a piston chamber containing a piston in sealed relationship with said piston chamber and moveable in one direction for forming a vacuum in said piston chamber, said piston being adapted to be locked in a position producing a fixed vacuum in said piston chamber.

19. The system of claim 8, further including means for calibrating said pressure transducer in relation to the vacuum induced in said vacuum chamber by said means for inducing a vacuum.

20. A pressure coupling means for use in a pressure monitoring assembly for monitoring pressure in a fluid line, comprising:

a disc body member including a fluid chamber connected to said fluid line and including a first flexible pressure transfer diaphragm forming one wall of said fluid chamber;

a main body member including a second flexible pressure transfer diaphragm placed in sealing engagement with said first diaphragm and forming an intermediate vacuum chamber for communicating pressure changes in said fluid line from said first diaphragm to said second diaphragm, and means for inducing a vacuum in said vacuum chamber, for maintaining said first and second diaphragms in constant sealing engagement.

21. The system of claim 20, further including a pressure transfer chamber coupling said second diaphragm to a pressure transducer.

22. The system of claim 21, wherein said pressure transfer chamber is filled with a substantially incompressible fluid for communicating said pressure changes from said second transfer diaphragm to said pressure transducer.

23. The system of claim 22, wherein said fluid in said pressure transfer chamber is gelatinous.

24. The system of claim 20, further including means for sealing said vacuum chamber between said first and second diaphragms.

25. The system of claim 20, further including a vent channel connecting said vacuum chamber to a vacuum source.

26. The system of claim 24, wherein said vacuum source includes means for producing a constant vacuum in said vacuum chamber.

27. The system of claim 21, further including means for biasing said first and second diaphragm together in sealing engagement.

28. The system of claim 21, wherein said fluid chamber comprises a fluid channel having an inlet connected to an IV fluid line, and an outlet connected to the IV fluid line.

29. The system of claim 22, further including a reference air vent through said main body portion communicating ambient pressure to said pressure transducer.

30. The system of claim 21, wherein said means for inducing a vacuum comprises a piston chamber containing a piston in sealed relationship with said piston chamber and moveable in one direction for forming a vacuum in said piston chamber, said piston being adapted to be locked in a position producing a fixed vacuum in said piston chamber.

* * * * *

UNITED STATES PATENT AND TRADEMARK OFFICE
CERTIFICATE OF CORRECTION

PATENT NO. : 4,923,444
DATED : May 8, 1990
INVENTOR(S) : Adib G. Daoud et al.

It is certified that error appears in the above-identified patent and that said Letters Patent is hereby corrected as shown below:

Column 5, line 41:
Claim 8, line 15, change "including" to --inducing--.

Claim 8, line 15, delete "in said" (second occurrence).
Column 5, line 42:
Claim 8, line 16, delete "vacuum".

Signed and Sealed this

Twenty-eighth Day of July, 1992

Attest:

DOUGLAS B. COMER

Attesting Officer

Acting Commissioner of Patents and Trademarks